(12) United States Patent
Kiliaan et al.

(10) Patent No.: US 7,560,447 B2
(45) Date of Patent: Jul. 14, 2009

(54) PREPARATION FOR THE PREVENTION AND/OR TREATMENT OF VASCULAR DISORDERS

(75) Inventors: Amanda Johanne Kiliaan, Wageningen (NL); Robert Johan Joseph Hageman, Waddinxveen (NL)

(73) Assignee: N.V. Nutricia, Zoetermeer (NL)

(*) Notice: Subject to any disclaimer, the term of this patent is extended or adjusted under 35 U.S.C. 154(b) by 0 days.

(21) Appl. No.: 11/741,547

(22) Filed: Apr. 27, 2007

(65) Prior Publication Data

US 2007/0202194 A1 Aug. 30, 2007

Related U.S. Application Data

(60) Division of application No. 09/703,798, filed on Nov. 2, 2000, now Pat. No. 7,226,916, which is a continuation-in-part of application No. 09/566,386, filed on May 8, 2000, now abandoned.

(51) Int. Cl.
*A61K 31/60* (2006.01)
*A61K 31/20* (2006.01)
*A61K 36/16* (2006.01)

(52) U.S. Cl. .................. 514/165; 514/494; 514/560; 514/551; 424/725; 424/752; 530/350

(58) Field of Classification Search ............ 514/165, 514/494, 822, 560, 551; 424/725, 752; 530/350
See application file for complete search history.

(56) References Cited

U.S. PATENT DOCUMENTS

| | | | |
|---|---|---|---|
| 4,595,680 A | 6/1986 | della Valle et al. | |
| 4,810,497 A | 3/1989 | Horrobin | |
| 4,837,219 A | 6/1989 | Hutterer | |
| 5,004,615 A | 4/1991 | Glick | |
| 5,077,069 A | 12/1991 | Chang et al. | |
| 5,108,767 A | 4/1992 | Mulchandani et al. | |
| 5,177,082 A | 1/1993 | Yu et al. | |
| 5,223,285 A | 6/1993 | DeMichele et al. | |
| 5,234,702 A | 8/1993 | Katz et al. | |
| 5,308,832 A | 5/1994 | Garleb et al. | |
| 5,401,730 A | 3/1995 | Sauvage et al. | |
| 5,753,703 A | 5/1998 | Cavazza et al. | |
| 5,837,701 A * | 11/1998 | Bleiweiss et al. ........... | 514/217 |
| 5,885,608 A | 3/1999 | McEntee | |
| 5,886,037 A | 3/1999 | Klor et al. | |
| 5,922,704 A | 7/1999 | Bland | |
| 6,008,221 A | 12/1999 | Smith et al. | |
| 6,069,138 A | 5/2000 | Ponroy | |
| 6,120,814 A | 9/2000 | Highman et al. | |

FOREIGN PATENT DOCUMENTS

| | | |
|---|---|---|
| DE | 4309217 A1 | 7/1994 |
| EP | 0 213 724 | 3/1987 |
| EP | 0 652 012 | 10/1995 |
| EP | 696.453 | 2/1996 |
| EP | 0 711 559 B1 | 5/1996 |
| EP | 0 721 742 | 7/1996 |
| EP | 721.742 | 7/1996 |
| EP | 754.001 | 1/1997 |
| EP | 914.111 | 5/1999 |
| EP | 1.061.887 | 7/2000 |
| EP | 1.106.181 | 6/2001 |
| FR | 2 773 484 | 7/1999 |
| JP | 1990-302732 | 8/1990 |
| JP | 1995-224142 | 6/1995 |
| JP | 1996-252856 | 5/1996 |
| JP | 1998-140919 | 1/1998 |
| JP | 1998-406051 | 6/1998 |
| JP | 1997-424744 | 6/1999 |
| JP | 2000-148134 | 11/1999 |
| WO | WO 88/09171 | 12/1988 |
| WO | WO 93/19624 | 10/1993 |
| WO | WO 94/27628 | 12/1994 |
| WO | WO 97/39749 | 10/1997 |
| WO | WO 98/32428 | 7/1998 |
| WO | WO 98/33494 | 8/1998 |
| WO | WO 99/03365 | 2/1999 |
| WO | WO 99/11625 | 3/1999 |
| WO | WO 99/21565 | 5/1999 |
| WO | WO 99/53777 | 10/1999 |
| WO | WO 01/03696 | 1/2001 |

OTHER PUBLICATIONS

Fugh-Berman et al., "Dietary supplements and natural products as psychotherapeutic agents". Psychosomatic Medicine 61:712-728. 1999.

Chang, S.J., Nutrition Research, 1999, 19(11), 1613-1624: "Vitamin B6 Protects Vascular Endothelial Injury by Activated Platelets."

* cited by examiner

*Primary Examiner*—Ruth A Davis
(74) *Attorney, Agent, or Firm*—Gilberto M. Villacorta; Sunit Talapatra; Foley & Lardner LLP

(57) ABSTRACT

The present invention relates to a preparation suitable for the prevention and/or treatment of vascular disorders, comprising the following fractions:
  fraction a) consisting of long chain polyunsaturated fatty acids;
  fraction b) consisting of phospholipids, which fraction contains at least two different phospholipids selected from the group consisting of phosphatidylserine, phosphatidylinositol, phosphatidylcholine and phosphatidylethanolamine.
  fraction c) consisting of compounds which are a factor in methionine metabolism, which fraction contains at least one member selected from the group consisting of folic acid, vitamin B12, vitamin B6, magnesium and zinc.

20 Claims, No Drawings

PREPARATION FOR THE PREVENTION AND/OR TREATMENT OF VASCULAR DISORDERS

This application is a division of U.S. application Ser. No. 09/703,798, filed Nov. 2, 2000, which is a continuation-in-part of U.S. application Ser. No. 09/566,386, filed May 8, 2000, the disclosures of which are incorporated by reference herein in their entireties.

BACKGROUND OF THE INVENTION

The present invention relates to preparations suitable for the prevention and/or treatment of vascular disorders. The invention also relates to the use of these preparations for the prevention and/or treatment of diseases that find their main cause in vascular problems, in particular dementia syndromes.

The vascular system in the human body is well described in the art. An important part of the system are the blood vessels, that generally are divided in arteries and veins, dependent whether they transport blood to or from the heart. They vary in size from large (e.g. the aorta) to very small (capillaries). From an anatomical point of view larger blood vessels in general comprise as observed from the lumen side:
1. the tunica intima, that consists of a smooth (mono)layer of endothelial cells and a subendothelial layer that consists of a loose layer of connective tissue,
2. the tunica media, which consists of a layer of (innervated) smooth muscle cells and elastic fibers, and
3. the tunica adventitia which is composed of loosely woven collagen fibers, which are infiltrated by tiny lymphatic and blood vessels.

The endothelial cells in the tunica intima are in direct contact with blood and have a barrier function for the underlying tissue. This barrier function includes selective transport of components from blood to the underlying tissue and vice versa, and protection of the underlying tissue. Endothelial cells get easily damaged due to a wide variety of causes like mechanic forces or interaction with stressor components such as classic anaphylatoxins, and components that may occur in the blood, such as homocysteine or components that result from treatment with certain types of drugs (e.g. chemotherapeutics). Vascular permeability can further be increased by a wide variety of humoral- and cell-derived mediators.

Endothelial dysfunction can result in a wide range of disorders. Damage to the endothelial layer can disturb the physiological functions thereof such as transport properties and expose the underlying tissue to stressors. Monocytes may migrate to these damaged spots, get caught by adhesion molecules, differentiate into macrophages, which, when activated, may start up an inflammatory reaction. Due to this reaction cytokines may be released, which may trigger the release of reactive oxygen species, or change coagulation behaviour of blood components. This may result in occurrence of plaques in the arteries, which may ultimately result in hypertension, atherosclerosis and (later) arteriosclerosis.

Atherosclerosis may lead to an impaired blood supply to tissue, which may then become ischaemic. This may lead to damage to cells and even apoptose of the cells that depend on the oxygen and nutrient supply via these blood vessels. Tissue that has become ischaemic may thus lose functional capacity.

Dementia syndromes are characterised by an abnormal high and progressive loss of functional capacity of the brain. This process may start relatively early in life, like the dementias that are associated with some forms of epileptics, encephalitis, Huntington's disease, the dementias that can be observed after intoxication by (chronic) alcohol or drug abuse and the dementias due to cerebrovascular accidents and some genetic forms of dementias (early onset dementias). It may also start relatively late in life such as in Alzheimer's disease (presenile dementia), in senile dementia and in atherosclerotic dementia. Dementias may develop suddenly, e.g. after an apoplectic event, or develop very slowly such as in senile dementia.

Alzheimer's disease is characterised by an early step of excision of the amyloid-beta peptide (AB) from the precursor protein (APP) that is present in the endosomes of neurons or other cells of the central nervous system. The AB peptide produced by beta-secretase (BACE) may diffuse outside the cell and polymerise into amyloid filaments, which in turn may develop into mature amyloid plaques, especially when chaperone molecules like protease inhibitors are present. The inflammatory response to the deposits of AB polymers and/or amyloid plaque may eventually lead to neuronal cell death and loss of cerebral function.

Dementia syndromes occur relatively frequently; about 10% of the elderly population in the Netherlands suffer from this disease and still no cure has been found to prevent or treat dementias. Treatment with drugs that increase brain levels of neurotransmitters like acetylcholine, serotonin or (nor)adrenaline are ineffective in the long term and the relatively high doses that often are administered could lead to undesirable side effects.

For the prevention and treatment of vascular disorders no suitable therapy is available either. Vascular disorders and the consequences thereof are a major cause of death in the Western countries. At present vascular disorders are treated by prescribing specific diets that are restricted in cholesterol, saturated fatty acids and in some cases sodium content and by administering drugs that are designed to lower blood pressure (e.g. diuretics), and plasma levels of cholesterol e.g. statins (or other compounds that are able to inhibit the activity of HMG-CoA reductase).

Though some of the treatments are indeed effective in treating part of the phenomena associated with vascular problems, the treatments are not 100% effective in solving the real problem (the cause) and they may demonstrate undesired systemic side effects.

PRIOR ART

Vascular endothelial cells and their function in the blood vessel have been studied for a long time. Many details about biochemical processes that occur in these cells have been published as well.

Recently Chang published in vitro data about the effect of pyridoxal-5-phosphate on human umbilical vein endothelial cells that "suggested that vitamin B6 protects endothelial cells by enhancing the beneficial function and preventing cell injury which are responsible for the initiation and the disease process of atherosclerosis". See Chang S. J. Nutrition Research, 1999, 19 (11), 1613-1624; "Vitamin B6 protects vascular endothelial injury by activated platelets".

Much literature has appeared about the aetiology of vascular diseases and dementia syndromes. Associations have been made between consumption of fruit on plasma levels of homocysteine or cholesterol and the presence of cardiovascular diseases.

The structure of cell membranes has been studied; many different components appear to be part of the membrane, such as lipids, proteins and cholesterol. Cholesterol appears to be important for the cell membrane. It decreases the fluidity of the outer cell membrane. It also is able to capture some radicals and is claimed to stop self-propagating radical chain reactions in the cell membrane. It is currently thought that vascular disorders should be treated with cholesterol lowering diets. However, it is not recognised that some forms of cholesterol, in particular plasma cholesterol, could be important in the repair mechanisms associated with vascular damage.

WO 99/11625 discloses the use of specific derivatives of huperzine A for inhibiting acetylcholine esterase for example in the treatment of Alzheimer's dementia and myasthemia gravis.

EP 0213724 discloses the use of phosphatidylcholine and phosphatidylethanolamine for membrane fluidisation.

Citric acid and/or citrates are widely used in food manufacture as taste modifier, acidifier and product stabiliser. U.S. Pat. Nos. 5,234,702 and 5,077,069 disclose the use of citric acid as a synergetic component for the antioxidant action of ascorbyl palmitate, beta-carotene and tocopherol.

WO 99/21565 discloses the use of any Kreb's cycle intermediate selected from citric acid, aconitic acid, isocitric acid, α-ketoglutaric acid, succinic acid, fumaric acid, malic acid and oxaloacetate or precursors thereof for treating disorders that are characterised by a decreased level of oxidative metabolism (page 5, line 25), in particular disorders of the nervous system but also of cardiovascular diseases. In particular precursors of oxaloacetate are preferred (page 7, line 10). No reference is made to beneficial effects of administration of these components on vasoendothelial cells, nor to additional effects that could be obtained by including phopholipids or LC-PUFA's in the composition.

EP 0 711 559 describes the use of phosphatidylserines for the manufacture of a medicament for improving cerebration, in particular for the treatment of Parkinson's disease and dementia such as Alzheimer's disease. The preparation according to this document contains phophatidyl-L-serine which has a structural fatty acid chain derived from at least one raw material lecithin as the effective ingredient. PCT/US88/01693 describes the use of phosphoethanolamine and related compounds for the use in the treatment of Alzheimer's disease.

SUMMARY OF THE INVENTION

The present inventors have now found a preparation for the treatment of vascular disorders that is effective because it provides activity on the function of the tunica intima and endothelial cells in general, which is important for influencing the aetiology and development of a wide range of vascular disorders and several other secondary disorders, in particular dementia syndromes.

Thus, the present invention provides a preparation suitable for the prevention and/or treatment of vascular disorders, comprising the following fractions:
  fraction a) consisting of long chain polyunsaturated fatty acids;
  fraction b) consisting of phospholipids, which fraction contains at least two different phospholipids selected from the group consisting of phosphatidylserine, phosphatidylinositol, phosphatidylcholine and phosphatidylethanolamine.
  fraction c) consisting of compounds which are a factor in methionine metabolism, which fraction contains at least one member selected from the group consisting of folic acid, vitamin B12, vitamin B6, magnesium and zinc.

The preparation of the invention can be a pharmaceutical, dietetic as well as a nutritional preparation. The products can have the form of a liquid, powder, bar, cookie, sweetie, concentrate, paste, sauce, gel, emulsion, tablet, capsule, etc. to provide the daily dose of the bioactive components either as a single or in multiple doses. The products can be packaged by applying methods known in the art, to keep the product fresh during shelf life and allow easy use or administration.

DETAILED DESCRIPTION OF THE INVENTION

The combined administration of these fractions results in the treatment and prevention of vascular disorders on different levels, in particular on the level of the tunica intima and endothelial cells in general. Fraction a) consists of long chain polyunsaturated fatty acids, preferably Ω-3 and/or Ω-6 fatty acids.

The function of fraction a) is to modulate inflammatory processes that may occur in vessel walls and cerebral tissue, to normalise plasma cholesterol levels, especially LDL-cholesterol levels and revert the atherosclerotic process and to increase fluidity of neuronal, erythrocyte and blood vessel membranes. It was found that especially a mixture of Ω-3 and Ω-6 long chain polyunsaturated fatty acids (LCPUFA's) should be included in a ratio of Ω-3 fatty acids to Ω-6 fatty acids of about 2.5 to 5.5 wt/wt.

Preferred Ω-3 LCPUFA's are eicosapentaenoic acid (EPA) and docosahexaenoic acid (DHA). Best results are obtained when DHA and EPA are included in about equimolar amounts, for example a ratio of DHA to EPA of 0.5 to 2 wt/wt. Preferred Ω-6 LCPUFA's are dihomogammalinolenic acid (DHGLA) and arachidonic acid (AA). These should be included in an amount of about one fourth of the amount of EPA and DHA, for example a ratio of [DHA+EPA] to [DHGLA+AA] of 2.5 to 5.5, preferably 3.3-4.7 wt/wt. The daily dosage of the total of EPA+DHA+DHGLA+AA is preferably at least 120 mg, more preferably at least 350 mg. Per daily dose the preparation in particular contains 20 to 2000 mg, preferably 50 to 1000 mg EPA, 50 to 2000 mg, preferably 200 to 1000 mg DHA and 50 to 2000 mg, preferably 100 to 1000 mg DHGLA.

Further LCPUFA's that can be present are linoleic and α-linoleic acid. However, the ratio of the total amount of EPA+DHA+DHGLA+AA to the total amount of linoleic and α-linoleic acid should be larger than 0.1 wt/wt, preferably larger than 0.2, most preferably larger than 0.4.

As described above fraction b) consists of at least two different phospholipids selected from the group consisting of phosphatidylserine, phosphatidylinositol, phosphatidylcholine and phosphatidylethanolamine. Preferably this fraction contains phosphatidylcholine, phosphatidylethanolamine and phosphatidylserine.

The function of this fraction is to provide a direct source of neuronal and endothelial cell phospholipids. It is highly preferred to include a mixture of phospholipids, especially with regard to the choline/ethanolamine moiety couple on the one hand, and the serine/inositol moiety couple on the other hand. For best results the ratio of (phosphatidylcholine and/or phosphatidylethanolamine) to (phosphatidylserine and/or phosphatidylinositol) is 0.5-20 (wt/wt). Per daily dose at least 0.2 g and preferably more than 1 g phospholipids should be administered, for example 4 g. When the product is meant to be used by patients suffering from dementia syndromes, the amount of phosphatidylserine per daily dose product should be at least 0.1 g for best results and preferably more than 0.5 g.

Another preferred characteristic of the preferred phospholipids is the LCPUFA moiety. It is preferred to use phospholipids which provide the LCPUFA's as described above. They can for example be prepared by applying interesterification methods known in the art using for example raw phospholipid mixtures and ingredients that are rich in the particular LCPU-FA's. Use of these specific phospholipids ensures a high activity next to a relatively stable product. In preparations for oral use it is not required to use higher organised lipid fractions such as sphingomyelines due to the high metabolic rates of this type of compound in the gut, gut epithelial cells and liver. Also, other lipids, that are essentially free from DHA, EPA, DHGLA or AA, such as neutral triglycerides are preferably not included in the phospholipid fraction or in relatively low amounts, e.g. less than 40% and in particular less than 5% of the lipid fraction. Phospholipids can originate from egg yolk or soy, and can be isolated by applying methods that are known in the art, for example acetone extraction and optionally applying subsequent chromatographic techniques or adsorption methods. The phospholipid fraction can also consist, where required, of mixtures of synthetic phospholipids and (extracts of) phospholipids of natural origin.

Fraction c) consists of compounds, which are a factor in methionine metabolism. Total methionine metabolism (TMM) has been described in EP 0 891 719. Though it is known that a proper functioning of TMM is mandatory for the endogenous biosynthesis of many crucial compounds such as S-adenosyl methionine (for creatine, carnitine, etc) and glutathion, and though one has found associations between the occurrence of vascular disorders with hyperhomocysteinaemia, the relevance of a proper functioning of total methionine metabolism for in particular the endothelial cell has not been recognised.

Fraction c consists of compounds which are a factor in methionine metabolism and contains at least one member selected from the group consisting of folic acid, vitamin B12, vitamin B6, magnesium and zinc. Preferably this fraction contains at least folic acid, in particular in an amount of at least 200 μg and most preferably more than 400 μg per daily dose. Folic acid is also meant to include physiological equivalents thereof such as pharmaceutically acceptable salts thereof, 5-methyltetrahydrofolate and polyglutamate forms thereof as occur naturally. It is most preferred that at least folic acid and vitamin B6 are included, while the largest part of the population will benefit if these components are simultaneously included. Vitamin B6 should be included in an amount of more than 2 mg, in particular more than 2.5 mg per daily dose. It is even more advantageous when this fraction contains all of the members of the above mentioned group. The fraction can further contain SAMe (S-adenosyl methionine), choline, betaine and/or copper. If fraction c) comprises zinc and copper, the weight ratio of zinc to copper is between 5 to 12. Choline and/or betaine can be included.

Besides the fractions a) to c) described above, the preparation according to the invention can contain a further fraction d) that consists of citrate. Citrate is also meant to include citric acid. The products according to the invention should have a pH between 3.0 and 7.5 and preferably between 5 and 7. Citrate should be administered in an amount of 0.5 to 30 g, preferably 1.5 to 10 g per daily dose, for example more than 2.4 g.

In the biochemistry literature one can find that citric acid, as well as some other compounds, provides reducing equivalents to the cytosol and participates in the "Krebs cycle", thus yielding NADH and energy in the mitochondriae. It is also known for a long time that citric acid helps regulate glycolyses by feedback inhibition of the phosphofructokinase reaction.

However, it is not recognised that for a proper functioning of vascular endothelial cells it is important to have at the same time sufficient amounts of ATP and reducing equivalents in the form of NADPH available in the cytosol of these cells and that citrate can ensure this to occur, and more effectively than a functional analog like a Krebs cycle intermediate like oxaloacetate, malic acid or fumarate.

It is advantageous to include huperzine A or functional analogues thereof (fraction e), especially in those products that are designed to be used for the prevention and treatment of dementia syndromes, especially in those phases of the disease where acetylcholine metabolism is severely impaired. Huperzine A should be included in amounts of 0.04 to 2, preferably 0.07 to 1, most preferably 0.08 to 0.5 mg per daily dose. As an analogue also an extract of certain herbs such as *Huperzia serrata* can be used, when standardised on huperzine A content and purity. An amount of 0.04 to 20 mg, preferably 0.07 to 2 mg per daily dose of such an extract can be used. Also lipophilic derivatives of huperzine A can be used, e.g. those obtained by modification of the primary and/or secondary amino groups.

According to the invention preparations that comprises a fraction a), a fraction b) and a fraction c) as described above together with huperzine and/or citrate are highly preferred since they have in some patients an unexpected higher activity than a product that comprises fraction a, b and c without huperzine and/or citrate.

The preparation preferably further contains a fraction f) consisting of one or more of carnitine, vitamin B1, vitamin B5 and coenzyme Q10 or functional analogues thereof. As functional equivalents of carnitine can be mentioned pharmaceutically acceptable salts thereof or alkanoyl and acyl carnitines [acetyl-L-carnitine], which are particularly useful, or mixtures thereof. Carnitine is advantageously included in products that are meant to be used for patients suffering from dementia syndromes. In these products preferably a lipophilic derivative is used as carnitine source. It is most preferred to use acetyl-L-carnitine. This component provides acetyl groups in the brain for biosynthetic purposes. Carnitine should be included in an amount of 0.1 to 3 g, preferably 0.2 to 1 g per daily dose. Vitamin B5 can be included for instance as calcium pantothenate or other stable form. Preferred dosages are 8 to 80 mg, preferably 12 to 40 mg per daily dose product.

For products that are meant to be used for treatment or prevention of further progression of dementia syndromes it is preferred to use a lipophylic thiamine source such as benfothiamine, allithiamine, fursulthiamine or octothiamine. A degeneration of cerebral function as is observed during Parkinson's and Huntington's disease can be retarded by the product according to the invention. In products for these types of patients it is advantageous to include also respectively taurine and gamma-amino butyric acid or derivatives thereof such as piracetam. If coenzym Q10 is included the amount can be 0.8 to 200 mg and preferably 5 to 70 mg. The amounts can be that low because of the beneficial effect of the phospholipids on the membrane function.

Also a fraction g) can be present that provides anti-oxidant properties. Fraction g) consists of antioxidants selected from vitamin C, vitamin E, lipoic acid, selenium salts and carotenoids. A fraction h) consists of an extract of gingko biloba. This extract is obtained from the leaves and is enriched in flavonoids and especially terpenoids, in particular ginkgolides. It appears for example that an extract that comprises at least 4% ginkgolides is effective.

The preparation preferably contains the above components of the different fractions in an amount above the recommended daily intake. Per daily dose the preparation of the invention preferably comprises:

at least 120 mg long chain polyunsaturated fatty acids;

at least 200 mg phospholipids;

at least 200 µg folic acid; and at least 0.5 g citrate.

More preferably, the preparation comprises per daily dose:

at least 20 mg, preferably at least 50 mg eicosapentaenoic acid at least 50 mg, preferably at least 200 mg docosahexaenoic acid at least 50, mg preferably at least 100 mg arachidonic acid at least 200 mg, preferably at least 1000 mg phosphatidylserine, at least 200 µg, preferably at least 400 µg folic acid at least 100 mg, preferably at least 200 mg magnesium at least 5 mg, preferably at least 10 mg zinc at least 2 mg, preferably at least 2.5 mg vitamin B6 at least 2 µg, preferably at least 4 µg vitamin B12 at least 1.0 g, preferably at least 1.5 g citrate.

The preparations according to the invention can be used in the treatment and/or prevention of vascular, cardio- and cerebrovascular disorders and a selected range of secondary problems. The nature and impact of the latter depends on the time pattern and degree of decrease of the blood flow and the function of the organ/tissue that is involved. Damage to the endothelial cells may also lead to loss of elasticity and even a local lesion of the blood vessel.

Examples of problems of the cardiovascular system are atherosclerosis obliterans, angina pectoris, myocard infarct, cerebral vascular accidents, thrombosis, M. Bürger, varices, thrombo-phlebitis and the syndrome of Raynaud. Damage to endothelial cells may also lead to a localized vasoconstriction. When damage to the endothelial cells has a more systemic nature this may lead to increased blood pressure. Other vascular disorders that could be treated with the product are atherosclerosis, arteriosclerosis, hypercholesterolaemia, hyperlipidaemia, elevated blood pressure, angina pectoris, cerebrovasular accidents, temporary disorders associated with ischaemia, vene thrombose, postpartum thrombose, myocard infarct, varicose veins (varices), thrombo angiitis obliterans and atheroslecrosis obliterans.

Secondary problems that are treatable with the product are some problems that occur after mechanic traumata, such as those that occur in accidents, during or after labor and during surgery. Other examples of treatable secondary problems are problems with hearing loss (especially that associated with chemotherapy or ageing), with improper functioning of liver, stomach, kidneys, legs, lung, or prostate and sudden (cerebrovascular incident) or chronic decrease of cerebral functions. An especially preferred use is in the prevention of cognitive degeneration in persons at risk for Alzheimer's disease or vascular dementia.

We believe that many of the dementia syndromes find their basic cause in cardiovascular disorders. An effective blood supply would provide sufficient amounts of nutrients to the brain, which supports anti-inflammatory response to deposits of AB peptide polymer and helps degrade plaques. An adequate blood supply further can help prevent the degenerative oxidative processes that are observed in many neurological disorders such as in Parkinson's disease (in the substantia nigra) and supports biosynthesis and metabolism of neurotransmitters such as gamma-amino butyric acid and dopamine.

Example 1

Capsule for use by demented persons three times a day.
The capsule is prepared using methods known in the art and comprises as active components:

| | |
|---|---|
| DHA | 50 mg |
| EPA | 75 mg |
| phospholipids* | 250 mg |
| folic acid | 200 µg |
| vitamin B12 | 25 mg |
| Huperzia serrata | 100 ug |
| vitamin B1 | 100 mg |
| coenzym Q10 | 10 mg |
| vitamin E | 200 mg |
| Gingko biloba | 120 mg |

*phosphatidylcholine 130 mg, phosphatidylserine 120 mg (synthetic)

Example 2

Pudding for improvement of vascular conditions and secondary disorders such as dementia syndromes. The pudding is based on cow's milk, starch, sugar and flavourings prepared by methods known in the art and comprises as active ingredients per serving of 200 ml:

| | |
|---|---|
| phospholipids from egg | 4 g |
| (provides about 20 mg DHA | |
| and 20 mg AA and phospholipids | |
| comprise about 77% | |
| phosphatidylcholine and | |
| 16% phosphatidylethanolamine) | |
| phosphatidylserine | 100 mg |
| encapsulated fish oil | 0.3 g |
| (provides about 30 mg DHA and 30 mg EPA) | |
| Single cell oil (25 mg AA) | 0.06 g |
| folic acid (synthetic monoglutamate) | 0.3 mg |
| vitamin B6 (pyridoxine) | 3 mg |
| zinc (ZnSO4) | 10 mg |
| magnesium (MgO) | 100 mg |
| vitamin B12 (cyanocobalamine) | 3 µg |
| citrate/citric acid | 1.2 g |
| thiamine HCl | 2 mg |
| vitamin E | 20 mg |
| manganese (MnO) | 10 mg |

Example 3

Powdered concentrate that consists of the active components as given in example 2 and further 0.1 g orange flavouring and maltodextrine to make up a total mass of 10 g. This amount is packed in a sachet and can be used to be reconstituted in any drink (milk, fruit juice, etc.).

Example 4

Powder for improvement of vasoendothelial function consisting of

| | |
|---|---|
| soylecithin* | 3 g |
| folic acid | 400 µg |
| vitamin B6 | 3 mg |
| vitamin B12 | 4 µg |

-continued

| | |
|---|---|
| zinc | 15 mg |
| magnesium | 150 mg |
| citric acid/citrate (pH of product 7.0) | 2.2 g |
| maltodextrines | to make up a total weight of 10 g |

*phosphatidylcholine:phosphatidylethanolamine:phosphatidylinositol = 24:22:15)

Example 5

Muesli-bar of about 25 g based on sugar, cereals and pieces of dried fruit that comprises as active components:

| | | |
|---|---|---|
| soylecithin* | 2 | g |
| encapsulated fish oil | 0.6 | g |
| SCO (AA) | 0.3 | g |
| Folic acid | 400 | µg |
| pyridoxamine | 3 | mg |
| cyanocobalamine | 5 | µg |
| zinc oxide | 30 | mg |
| magnesium oxide | 200 | mg |
| citric acid/citrate pH 6.5 mixture | 2 | g |
| Huperzine serrata extract | 150 | µg |
| Gingko biloba extract | 200 | mg |
| calcium sulphate | 300 | mg |
| vitamin D | 10 | µg |

*phosphatidylcholine:phosphatidylethanolamine:phosphatidylinositol = 45:26:14)

The bar is coated with a layer of chocolate.

The invention claimed is:

1. A method for treating a person suffering from dementia syndrome or being at risk of developing dementia syndrome, comprising administering to the person a preparation comprising:
   a) long chain polyunsaturated fatty acid fraction comprising eicosapentaenoic acid (EPA) and docosahexaenoic acid (DHA);
   b) at least two phospholipids selected from the group consisting of phosphatidylserine, phosphatidylinositol, phosphatidylcholine and phosphatidylethanolamine; and
   c) folic acid, and vitamin B6 wherein the preparation comprises 120-2000 mg per daily dosage of EPA and DHA collectively, of which at least 50 mg of the daily dosage is DHA.

2. The method according to claim 1, wherein the preparation comprises 50-2000 mg per daily dosage of DHA.

3. The method according to claim 1, wherein the folic acid is present in an amount of at least 200 µg per daily dosage.

4. The method according to claim 1, wherein the vitamin B6 is present in an amount of at least 2 mg per daily dosage.

5. The method according to claim 1, wherein the preparation comprises at least 2 µg of vitamin B12 per daily dosage.

6. The method according to claim 1, wherein the preparation comprises phosphatidylcholine, phosphatidylethanolamine and phosphatidyl serine.

7. The method according to claim 1, wherein the preparation comprises at least 0.2 g phospholipids.

8. The method according to claim 1, wherein the preparation comprises at least 0.1 g phosphatidylserine.

9. The method according to claim 1, wherein the preparation further comprises linoleic acid, α-linolenic acid, or both.

10. The method according to claim 9, wherein the preparation further comprises dihomogammalinolenic acid (DHGLA), arachidonic acid (AA), or both.

11. The method according to claim 10, wherein the ratio of the total amount of EPA+DHA+DHGLA+AA to the total amount of linoleic acid and α-linolenic acid is larger than 0.1:1.

12. The method according to claim 11, wherein the ratio of the total amount of EPA+DHA+DHGLA+AA to the total amount of linoleic acid and α-linolenic acid is larger than 0.4:1.

13. The method according to claim 1, wherein the preparation further comprises at least one of a citrate or citric acid.

14. The method according to claim 1, wherein the preparation further comprises huperzine A.

15. The method according to claim 1, wherein the preparation further comprises S-adenosylmethionine, choline, betaine, copper, or a combination thereof.

16. The method according to claim 1, wherein the preparation further comprises zinc and copper in a weight ratio of zinc to copper between 5 and 12.

17. The method according to claim 1, wherein the preparation further comprises carnitine, vitamin B1, vitamin B5, coenzyme Q10, or a combination thereof.

18. The method according to claim 1, wherein the preparation further comprises an antioxidant selected from the group consisting of vitamin C, vitamin E, lipoic acid, selenium salts and carotenoids.

19. The method according to claim 1, wherein the preparation further comprises an extract of ginkgo biloba.

20. The method according to claim 1, wherein the dementia syndrome is Alzheimer's disease.

* * * * *